(12) United States Patent
Yatomi et al.

(10) Patent No.: US 6,562,342 B1
(45) Date of Patent: May 13, 2003

(54) PREVENTIVES/REMEDIES FOR INFLAMMATORY INTESTINAL DISEASE

(75) Inventors: Takehiro Yatomi, Tokyo (JP); Shigekazu Nagata, Minoo (JP); Takashi Suda, Kanazawa (JP)

(73) Assignees: Mochida Pharmaceutical Co., Ltd., Tokyo (JP); Osaka Bioscience Institute, Osaka (JP)

( * ) Notice: Subject to any disclaimer, the term of this patent is extended or adjusted under 35 U.S.C. 154(b) by 0 days.

(21) Appl. No.: 09/601,455

(22) PCT Filed: Feb. 5, 1999

(86) PCT No.: PCT/JP99/00496
§ 371 (c)(1),
(2), (4) Date: Aug. 2, 2000

(87) PCT Pub. No.: WO99/39737
PCT Pub. Date: Dec. 8, 1999

(30) Foreign Application Priority Data

Feb. 6, 1998 (JP) ............................................. 10-025492

(51) Int. Cl.⁷ ............................................. A61K 39/395
(52) U.S. Cl. ............................... 424/133.1; 424/145.1; 424/152.1; 424/158.1; 424/172.1
(58) Field of Search ........................... 424/145.1, 130.1, 424/133.1, 142.1, 152.1, 158.1, 172.1

(56) References Cited

U.S. PATENT DOCUMENTS 6,096,312 A * 8/2000 Nakamura et al. ....... 424/145.1
6,348,334 B1 2/2002 Nagata et al.

FOREIGN PATENT DOCUMENTS

| EP | 0842948 | 5/1998 |
| WO | WO9513293 | 5/1995 |
| WO | WO9702290 | 1/1997 |
| WO | WO9818487 | 5/1998 |

OTHER PUBLICATIONS

Ono et al. Abstracts of 83rd Meeting of Japanese Society of Gastroenterology, p. 243, Intestine–56, 1997.*
Ueyama et al. 1998. Gut 43(1):48–55.*
Kneitz, Burkhard et al., Eur. J. Immunol. vol. 25 (1995) pp. 2572–2577.
Sträter, J. et al., Gastroenterology, vol. 113 (1997) pp. 160–167.
Igaku–no, Ayumi, Progress in Med., vol. 178, No. 9 (1996) p. 651.
De Maria, R. et al., J. Clin. Invest., vol. 97, No. 2 (1996) pp. 316–322.
Iwamoto, M. et al., J. Pathology, vol. 180 (1996) pp. 152–159.
Lúdvíksson, B. et al., J. of Immuno., vol. 158 (1997) pp. 104–111.
Sadlack, B. et al., Cell, vol. 75 (1993) pp. 253–261.
Parr, E. et al., Cell & Tissue Research, vol. 290 (1997) pp. 21–29.
Parr et al., Cell and Tissue Research, vol. 290, No. 1, pp. 21–29 (1997).

* cited by examiner

*Primary Examiner*—Mary E. Mosher
(74) *Attorney, Agent, or Firm*—Birch, Stewart, Kolasch & Birch, LLP

(57) ABSTRACT

Preventives/remedies for at least one disease selected from the group consisting of inflammatory intestinal disease, ischemic colitis and idiopathic inflammatory intestinal disease induced by infection, chemicals and radiation which contain as the active ingredient an anti-Fas ligand antibody; and preventives and remedies with the use of the same.

6 Claims, 2 Drawing Sheets

PREVENTIVES/REMEDIES FOR INFLAMMATORY INTESTINAL DISEASE

This application is the national phase under 35 U.S.C. §371 of PCT International Application No. PCT/JP99/00496 which has an International filing date of Feb. 5, 1999, which designated the United States of America.

TECHNICAL FIELD

This invention relates to preventives and remedies for inflammatory intestinal disease which contain an anti-Fas ligand antibody as their effective component.

BACKGROUND ART

Fas is a cell surface antigen which transmits apoptosis signal to the cell, and Fas is recognized by Fas antibody (Yonehara, S. et al., J. Exp. Med., vol. 169, 1747–1756, 1989) which is a monoclonal antibody produced by immunizing a mouse with human fibroblast. Fas gene was recently cloned by Itoh, N. et al., and it was then found out that Fas is a cell membrane protein of about 45 kD, and from the amino acid sequence, it was revealed that Fas is a member of TNF receptor family (Cell, vol. 66, pages 233–243, 1991). Mouse Fas gene was also cloned (Watanabe-Fukunaga, et al., J. Immunol., vol. 148, pages 1274–1279, 1992), and the expression of Fas mRNA in thymus, liver, lung, heart, ovary was confirmed.

Human Fas ligand is a polypeptide which has been reported by Nagata et al. to be a biological molecule which induces apoptosis of Fas-expressing cells (Takahashi, T. et al., International Immunology, vol. 6, pages 1567–1574, 1994). Human Fas ligand is a glycosilated Type II membrane protein of TNF family with a molecular weight of about 40 kD. As in the case of TNF, human Fas ligand in the human body is estimated to be in the form of a trimer (Tanaka, M. et al., EMBO Journal, vol. 14, pages 1129–1135, 1995). The extracellular domain of the human Fas ligand is highly homologous with the extracellular domain of rat Fas ligand (Suda, T. et al., Cell, vol. 75, pages 1169–1178, 1993) and mouse Fas ligand (Takahashi, T. et al., Cell, vol. 76, pages 969–976, 1994). The human Fas ligand recognizes not only the human Fas but also the mouse Fas to induce the apoptosis, and vice versa, the rat Fas ligand and the mouse Fas ligand also recognize the human Fas to induce the apoptosis. Shirakawa, K. et al. has produced an anti-Fas ligand antibody, and disclosed an assay method for measuring Fas ligand in human body fluids using the thus produced antibody (International Patent Application Publication No. WO 97/02290).

Considerable researches have also been done on the mechanism of signal transduction in the cell upon the Fas-mediated apoptosis, and identification and cloning of the factors which interacts with the intracellular domain of the Fas, in particular, the region called "death domain" to transmit or block the signal have been reported. Possibility of the involvement of interleukin-1-converting enzyme (ICE)-related thiol proteases in the signal transduction of the Fas-mediated apoptosis has also been indicated.

Possibility of the involvement of the Fas/Fas ligand system in functions other than the apoptosis has also been indicated, for example, the possibility of the function that the Fas/Fas ligand system act with neutrophil to induce inflammation has also been indicated (Kayagaki, N. et al., Rinshou Men-eki (Clinical Immunology), vol. 28, pages 667–675, 1996).

Relationship of the apoptosis, in particular, the Fas-mediated apoptosis with various diseases and physiological phenomena has been recently indicated. For example, possibility has been indicated for involvement of abnormal Fas-mediated apoptosis in the death of hepatocytes in viral fulminant hepatitis, in some types of autoimmune diseases, and the like. Also disclosed is a therapeutic drug for hepatitis containing an anti-human Fas ligand antibody as its effective component (JP-A 1997-124509).

Inflammatory intestinal disease may be etiologically categorized into specific disease and nonspecific disease. The phanerogenic specific diseases include inflammatory intestinal disease induced by infection, drugs, chemicals and radiation, and ischemic colitis. The nonspecific disease is called idiopathic inflammatory intestinal disease, and typical such diseases are Crohn's disease and ulcerative colitis, both of which are cryptogenic, intractable, chronic intestinal diseases which experience active and remissive stages. Although ulcerative colitis is cryptogenic, involvement of immunopathological mechanisms and psychological factors in the ulcerative colitis have been indicated. The patients of ulcerative colitis are mainly adults of under 30 although infants and adults over 50 occasionally suffer from ulcerative colitis. The ulcerative colitis is an inflammatory disease of intestine, and more specifically, an inflammatory disease of rectum, and mucous membrane and its substratum are the main lesions. This disease is generally associated with hemorrhagic diarrhea and systemic conditions of varying degree, and when the patients suffer from this disease for a prolonged period and the lesion extends to the entire intestine, the lesion is likely to undergo transformation. Crohn's disease is a cryptogenic disease and the patients are mainly young adults. The Crohn's disease is associated with granulomatous inflammation lesion exhibiting edema, fibrosis (myofibrosis), and ulcer, and such lesion may occur in various parts of the digestive tract. Metastatic lesion is occasionally found in places other than the digestive tract (in particular, in skin). The Crohn's disease was previously called terminal ileitis associated with the lesion in the terminal ileum. However, it has been clearly found that this disease may occur at every parts of the digestive tract from oral cavity to anus. The clinical image of the Crohn's disease varies depending on the place of the lesion and its coverage, and the disease is typically associated fever, malnutrition, anemia, arthritis, iritis, liver damage and other systemic complications (Takazoe, M. et al., Naika (Internal Medicine), vol. 77, No.2, pages 257–264, 1996).

With the progress in immunology and molecular biology, etiology of idiopathic inflammatory disease has been widely investigated and gradually clarified from the points of MHC class II of inflammatory cells such as lymphocyte and epithelial cell, cytokines, adhesive molecules, inflammatory substances such as arachidonic acid and leukotriene, active oxygen, etc. The detailed etiology, however, is yet unknown. In view of such uncertainty in the mechanism of its onset, it is impossible to conduct an etiological therapy for the inflammatory intestinal disease as a routine clinical practice, and the therapies presently conducted are nonspecific therapies (Matsuhashi, N. et al., Naika (Internal Medicine), vol. 77, No.2, pages 227–229, 1996). Current standard therapy for the inflammatory intestinal disease is symptomatic treatment using salazosulfapyridine, steroids, and the like (Current Therapy for Disease in Digestive Apparatus, '95–'96, pages 175–182, 1995). Salazosulfapyridine, however, suffers from side effects such as nausea, headache, fever, rash, hemolytic anemia, epidermolysis, granulocytopenia, fibrous alveolitis, headache, pancreatitis, and male infertility (Allegayer et al., Gastrointestinal pharmacology, vol. 24, pages 643–658, 1992). Steroids also suffer from various serious side effects (Kashiwazaki, S. et al., Sogo Rinsho (General Clinical Medicine), vol. 43, 1725–1729, 1994). Thus, salazosulfapyridine and steroids need careful managements in their timing, dose, duration of administration.

Iwamoto et al. has reported expression of Fas/Fas ligand in epithelium of intestinal crypt of the patient suffering from ulcerative colitis (J. Pathology, vol. 180, pages 152–159, 1996). Ruggero De Maria et al. has reported expression of Fas ligand on T cell of tunica propia of human intestinal mucous membrane (J. Clin. Invest. vol. 97, pages 316–317, 1996). Jorn Strater et al. has reported that epithelial cell of intestinal mucous membrane from the patient suffering from ulcerative colitis exhibits resistance to apoptosis by TNF while its exhibits sensitivity to the apoptosis by anti-human Fas antibody, CH-11; that Fas ligand is expressed in interstitial lymphocytes of the intestine; and that increase in apoptosis of colonocyte and expression of the Fas ligand are found in ulcerative colitis (Gastroenterology, vol. 113, 160–167, 1997). In the meanwhile, there have been reported that the mechanism of Fas-mediated cell death is far from being dominant in cytotoxicity of intestinal epithelial cell from the patient suffering from ulcerative colitis and some other courses of cytotoxicity should be present (Abstracts of 83rd Meeting of Japan Gastroenterology Society, page 243, Entero-56, 1997), and that while expression of Fas/Fas ligand was found together with the presence of the apoptotic cell in the case of ulcerative colitis, expression of Fas/Fas ligand was not recognizable in the epithelium of crypt in the case of the other inflammatory intestinal diseases such as Crohn's disease and enteritis induced by drug or radiation, and the like (Igaku-no Ayumi (Progress in Medicine), vol. 178, pages 651–654, 1996). In addition, there has been reported that knockout mouse of interleukin-2 exhibited symptoms similar to human inflammatory intestinal disease (Sadlack, B. et al., Cell, vol. 75, pages 253–261, 1993), and the reports using this model (Burkhad, K. et al., Eur. J. Immunol., vol. 25, pages 2572–2577, 1995; Ludviksson, B. R. et al., J. Immunol., vol. 158, pages 104–111, 1997) indicate that inhibition of the Fas-mediated apoptosis is the etiology for the inflammatory intestinal disease. As described above, the issue of the involvement of the Fas/Fas ligand-mediated apoptosis in the inflammatory intestinal disease such as ulcerative colitis and Crohn's disease has been a divisive question among the workers in the field, and no unified view has been established as to whether the apoptosis is involved in the pathology or not, and if involved, whether the pathology is caused by the induction of the apoptosis or by the inhibition of the apoptosis. As described above, involvement of direct or indirect Fas/Fas ligand-mediated apoptosis in the onset of the pathology of the inflammatory disease is yet unknown.

The report of the anti-Fas ligand antibody (International Patent Application Publication No. WO 97/02290), supra describes that such antibody may be effective in preventing or treating the diseases such as ulcerative colitis and Crohn's disease wherein the involvement of the Fas/Fas ligand has been indicated. As in the case of such report, it has been possible to postulate the effectivity of the anti-Fas ligand antibody in ulcerative colitis and Crohn's disease. The postulation, however, was supported with no specific data or grounds, and there are also reports which are contradictory to such postulation. In short, effectivity of the anti-Fas ligand antibody in the inflammatory intestinal disease such as ulcerative colitis and Crohn's disease is yet unknown. There has also been reported that an agonist for γ-retinoic acid receptor and artificial veto cell which have apoptosis-inducing action are effective in treating the Crohn's disease (International Patent Application Publication No. WO 97/13505 and International Patent Application Publication No. WO 96/32140).

In view of the situation as described above, namely, the uncertainty of the involvement of the Fas/Fas ligand in the inflammatory intestinal disease such as ulcerative colitis and Crohn's disease and the presence of the report describing the effectivity of the apoptosis-inducing substance in the inflammatory intestinal disease, it has been utterly unknown whether the anti-Fas ligand antibody having the apoptosis-suppressing action is effective in the inflammatory intestinal disease such as ulcerative colitis and Crohn's disease, and demonstration of the effectivity has been eagerly awaited. Such demonstration could not be realized due to the absence of appropriate findings.

DISCLOSURE OF THE INVENTION

An object of the present invention is to provide a preventive and therapeutic agent for inflammatory intestinal disease which acts by the novel mechanism of suppressing apoptosis. More specifically, the present invention provides a preventive and therapeutic agent for inflammatory intestinal disease which contains an anti-Fas ligand antibody as its effective component and a therapeutic method wherein such agent is used.

The inventors of the present invention have conducted intensive studies on the relation between the apoptosis and the inflammatory intestinal disease in order to save those suffering from the inflammatory intestinal disease, and found that the pathology is improved in the model of inflammatory intestinal disease by the anti-Fas ligand antibody. The present invention has been completed on the bases of such finding.

Accordingly, the present invention is directed to a preventive and therapeutic agent as described below as well as a prophylactic and therapeutic method wherein such agent is used.

(1) A preventive and therapeutic agent for at least one disease selected from the group consisting of inflammatory intestinal disease induced by infection, drugs, chemicals and radiation, ischemic colitis, and idiopathic inflammatory intestinal disease containing an anti-Fas ligand antibody as its effective component.

(2) A preventive and therapeutic agent according to (1) wherein said anti-Fas ligand antibody is a humanized anti-Fas ligand antibody.

(3) A preventive and therapeutic agent according to (1) or (2) wherein said disease is idiopathic inflammatory intestinal disease.

(4) A preventive and therapeutic agent according to any one of (1) to (3) wherein said disease is at least one disease selected from Crohn's disease and ulcerative colitis.

(5) A preventive and therapeutic agent according to any one of (1) to (4) wherein said agent produces its therapeutic effects on said disease in its active stage.

(6) A preventive and therapeutic agent according to any one of (1) to (5) wherein said agent has an action selected from the group consisting of improvement in mucous lesion, improvement in intestine adhesion, and improvement of diarrhea.

(7) A preventive and therapeutic agent containing as its effective component an anti-Fas ligand antibody which has the effect of improving the pathology of inflammatory intestinal disease induced by a chemical or a drug or its model.

(8) A preventive and therapeutic agent according to (7) wherein said model is a model of inflammatory intestinal disease induced by TNBS.

BEST MODE FOR CARRYING OUT THE INVENTION

Figure 1:
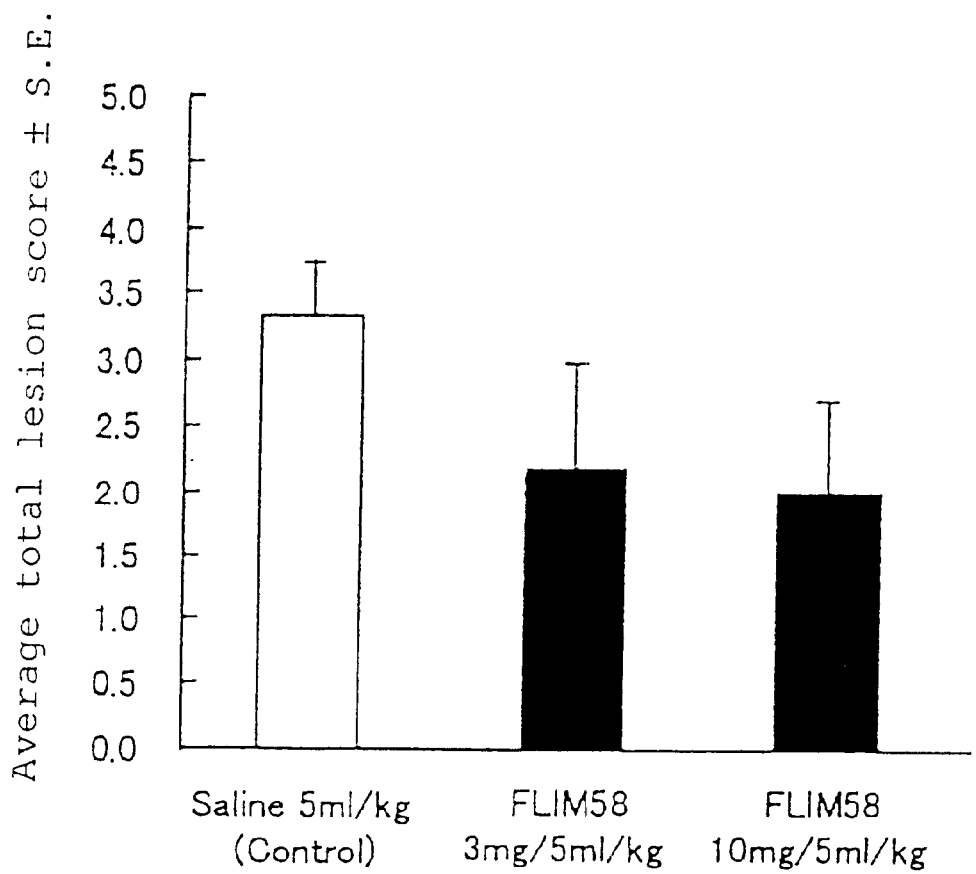
FIG. 1 is a view showing the effects of the anti-mouse Fas ligand antibody in improving the pathology of the model for the inflammatory intestinal disease. The white column and the black column stand for the control group and the group administered with the anti-mouse Fas ligand antibody, respectively.

The present invention is hereinafter described in further detail. The term "inflammatory intestinal disease" used in the specification designates at least one diseases selected from the group consisting of inflammatory intestinal disease induced by infection, drugs, chemicals and radiation, ischemic colitis, and idiopathic inflammatory intestinal disease.

The inflammatory intestinal disease which may be treated by the preventive and therapeutic agent of the present invention may be etiologically categorized into cryptogenic, idiopathic inflammatory intestinal disease, infectious inflammatory intestinal disease, drug-induced inflammatory intestinal disease, radiation-induced inflammatory intestinal disease, ischemic inflammatory intestinal disease, and other inflammatory intestinal diseases. The preventive and therapeutic agent of the present invention is preferably used in cryptogenic, idiopathic inflammatory intestinal disease.

Exemplary cryptogenic idiopathic inflammatory intestinal diseases include ulcerative colitis and Crohn's disease.

Exemplary infectious inflammatory intestinal diseases include Bechet's disease of intestinal type and vibrionic enteritis.

The drug-induced inflammatory intestinal disease may be further categorized by etiology into enteritis such as pseudomembranous colitis and MRSA enteritis caused by bacterial toxin in the use of an antibiotic, an antitumor agent, or an immunosuppressant and the like; enteritis such as hemorrhagic colitis caused by ischemic mechanism in the use of an antibiotic or a hormone agent and the like; enteritis caused by mucous membrane disorder due to inhibition of prostaglandin formation in the use of a non-steroidal anti-inflammatory, analgesic drug; and enteritis caused by direct local action of heavy metal agent.

Exemplary inflammatory intestinal diseases induced by radiation include radiation colitis.

Exemplary ischemic inflammatory intestinal diseases include ischemic colitis.

Examples of other inflammatory intestinal diseases include colonic diverticulosis (disease of colonic diverticula) and neonatal necrotizing enteritis.

In these diseases, an anti-Fas ligand antibody exhibits prophylactic and therapeutic effects by suppressing the apoptosis involved in each disease.

It should be noted that mammals other than human may also be treated by the agent of the present invention although the human is the most important object of the therapy.

The anti-Fas ligand antibody used in the present invention is not limited to any particular type although the antibody used is preferably the one whose antigen is the Fas ligand of the animal to be treated. For example, in the case wherein a human is treated, it is preferable to use an antibody whose antigen is the Fas ligand from human, namely, an anti-human Fas ligand antibody.

The anti-Fas ligand antibody used in the present invention is preferably a chimeric antibody or a humanized antibody. An exemplary preferable chimeric antibody which may be used for treating a human is a chimeric antibody comprising the variable region or the antigen-binding domain from a mouse antibody, and the constant region or the effecter domain from the human antibody. An exemplary preferable humanized antibody which may be used for treating a human is a humanized antibody wherein the constant region and the framework region (FR) are of human. origin, and the complementarity determining region (CDR) is of non-human origin. A non-human antibody is associated with biological defects when it is used in treating a human, for example, relatively short circulation half life, lack of developing various important functional properties of the immunoglobulin, and presence of immunogenicity. The chimeric antibody and the humanized antibody have obviated such defects.

The anti-Fas ligand antibody used in the present invention is preferably the one which suppresses the apoptosis of the Fas-expressing cell in an appropriate assay, for example, in the assay described in International Patent Application Publication No. WO 95/13293. It should be noted that the patent publication cited herein is incorporated herein by reference.

The antibody used in the present invention may be either a polyclonal antibody or a monoclonal antibody, and the molecular species of the antibody used in the present invention is not particularly limited. The antibody used in the present invention may be either an antibody molecule of normal form or a fragment thereof as long as the antibody used is capable of binding to the antigen to inhibit the Fas-mediated apoptosis. Exemplary antibody fragments include Fab, F(ab')$_2$, Fv, and single chain Fv (scFv) which is the Fv of heavy chain linked to the Fv of light chain by an adequate linker to form a single chain. In addition, the antibody used in the present invention may be an immunoglobulin of any class, subclass or isotype. As described above, the antibody used in the present invention is not limited to any particular type as long as it is capable of binding to the Fas ligand or the Fas to inhibit the biological actions of the Fas/Fas ligand system, and in particular, the Fas-mediated apoptosis.

The anti-Fas ligand antibody used in the present invention may be an antibody of any type (either monoclonal or polyclonal) and any origin produced by any appropriate process. The anti-Fas ligand antibody, however, is preferably a monoclonal antibody derived from a mammal. The monoclonal antibody used in the present invention may be produced in any animal species so long as it is a mammal which may be human or non-human. The monoclonal antibody from a mammal other than human may be the one from rabbit or other rodents. The non-limiting preferable examples of such rodents are mouse, rat and hamster, and use of such animals facilitates a convenient production of the monoclonal antibody. Furthermore, the monoclonal antibody is preferably the one which is capable of recognizing the antigen in a conventional immunoprocess such as radioimmunoassay, enzyme immunoassay, immunofluorescent analysis, or the like, and whose activity of suppressing the apoptosis of the Fas expressing cell is measurable by an appropriate assay procedure described in International Patent Application Publication No. WO 95/13293, and the like. Among these, an example of the most preferable anti-Fas ligand antibody is mouse F919-9-18 antibody produced by hybridoma F919-9-18 which was originally deposited on Jun. 22, 1995 in National Institute of Bioscience and Human Technology, Agency of Industrial Science and Technology (1–3, Higashi 1-chome, Tsukuba-shi, Ibaraki-ken, Japan) (Accession No. P-15002) and transferred from the original deposition to the international deposition on May 9, 1996 (Accession No. FERM BP-5535).

The anti-Fas ligand antibody used in the present invention may be prepared, for example, by the process described in International Patent Application Publication No. WO 95/13293 and International Patent Application Publication No. WO 95/02290.

When a monoclonal antibody is used in the present invention, such monoclonal antibody may be prepared by the process known in the art, for example, by using Fas ligand or a partial peptide thereof for the sensitized antigen, immunizing an animal with such antigen in accordance with a conventional process, fusing the resulting immunized cell with a known parent cell by a conventional cell fusion process, and screening for the monoclonal antibodyproducing cell by a conventional screening process.

More illustratively, the monoclonal antibody may be prepared by using the nucleotide sequence of the human Fas ligand disclosed in Takahashi, T. (International Immunology, vol. 6, pages 1567–1574, 1994). This nucleotide sequence may be inserted in a known expression vector system to transform an adequate host cell, the desired Fas ligand protein may be obtained and purified from the host cell or the supernatant, and the thus obtained purified Fas ligand protein may be used for the sensitized antigen.

The mammal which is immunized with the sensitized antigen is not limited to any particular type, and the mammal may be selected by considering the compatibility with the parent cell used in the cell fusion. Exemplary animals are mouse, rat, hamster, and rabbit.

The immunization of the animal with the sensitized antigen may be carried out by a known process. After the immunization and confirmation of the increase of the desired antibody in serum, the immunocytes are collected from the mammal, and subjected to cell fusion. The preferable immunocytes are splenic cells.

The parent cell to be fused with the immunocyte is not limited to any particular type. However, use of a known mammal myeloma cell line, and in particular, a mouse myeloma cell line such as P3 (P3x63Ag8.653) (J. Immunol. 123: 1548, 1978) is preferred. The cell fusion of the above-described immunocyte and the myeloma cell may be carried out basically in accordance with a known process such as the process of Milstein et al. (Milstein et al., Methods Enzymol. 73: 3–46, 1981).

The hybridoma is then screened for the one producing the target antibody used in the present invention and the monoclone is established by known procedures.

The monoclonal antibody is obtained from the thus prepared hybridoma producing the monoclonal antibody used in the present invention by such procedures as cultivating the hybridoma according to the conventional method and obtaining the monoclonal antibody from the supernatant; or transplanting the hybridoma to a mammal compatible with such hybridoma for propagation, and obtaining the monoclonal antibody from the ascite of the mammal. The former process is adapted for producing the monoclonal antibody of high purity, and the latter process is adapted for producing the monoclonal antibody in a large amount.

The monoclonal antibody produced by such process for use in the present invention may be further purified by a known purification means such as salting out, gel filtration, affinity chromatography, and the like.

The monoclonal antibody used in the present invention is not limited to the one produced by using a hybridoma, and may be the one produced by an antibody-producing cell immortalized by EBV and the like or the one produced by a genetic engineering process.

An exemplary such chimeric antibody which can be used in the present invention is a chimeric antibody comprising the variable region from the monoclonal antibody of a mammal other than human such as mouse, and the constant region from the human antibody. Such chimeric antibody may be produced by a known chimeric antibody production process, and in particular, by a genetic engineering process.

More preferably, the anti-Fas ligand antibody used in the present invention is a reshaped human antibody wherein CDR of the human antibody is replaced with the CDR derived from the antibody of a mammal other than human such as mouse. More illustratively, the constant region and the FR are preferably of human origin, and the CDR is preferably of non-human origin. A preferable example of the reshaped human antibody (humanized antibody) is humanized antibody having the CDR derived from the murine F919-9-18 antibody, which is disclosed in International Patent Application Publication No. WO 97/02290.

It should be noted that, if necessary, one or more amino acid in the FR in the variable region of the antibody may be substituted so that the CDR of the humanized antibody would form an adequate antigen-binding site.

The humanized antibody used in the present invention may be prepared in accordance with Leachman et al. (Nature 332: 323 (1988)) and European Patent Publication No. EP-A-0239400); Queen et al. (Proc. Natl. Acad. Sci. USA 86: 10029 (1989)), International Patent Application Publication Nos. WO 90/07861 and WO 92/11018); Co et al. (Proc. Natl. Acad. Sci. USA 88: 2869 (1991)); Co et al. (Nature 351: 501 (1991)); Co et al. (J. Immunol. 148: 1149 (1992)), and the like.

In the preventive and therapeutic agent for inflammatory intestinal disease of the present invention, a substance which suppresses the Fas-mediated apoptosis other than the anti-Fas ligand antibody may also be used in the same manner as the anti-Fas ligand antibody. Typical substances which suppresses the Fas-mediated apoptosis include Fas antagonists and substances which are capable of suppressing the binding between the Fas and the Fas ligand. The substance employed is not limited to any particular type as long as it blocks signal generation by the Fas or transduction of the thus generated signal at some stage to thereby suppress the function or the biological action of the Fas/Fas ligand system, and in particular, the apoptosis. The mechanism of such blockage may be inhibition of the action, function or expression of the Fas ligand or the Fas; interaction with the extracellular domain of the Fas ligand or the Fas; inhibition of the Fas ligand-Fas interaction; affecting the interaction between the cytoplasmic domain of the Fas and the cytoplasmic factor which interacts with the cytoplasmic domain of the Fas; inhibition of the activity of the cytoplasmic factor (for example, ICE-like protease) which is involved in the signal transduction of the Fas-mediated apoptosis, and the like. The apoptosis-suppressing substance may comprise either a high protein polymer or a low molecular weight compound.

Exemplary such substances include a Fas derivative; an anti-Fas antibody; an antisense oligonucleotide for the gene or its mRNA of the Fas or the Fas ligand; a substance which interacts with the cytoplasmic domain of the Fas; and an ICE inhibitor.

The Fas derivative is not limited to any particular type as long as it is capable of binding at least with the Fas ligand, or capable of inhibiting the Fas ligand-mediated apoptosis. The Fas derivative may also be the one which comprises an amino acid sequence of a known Fas that has been arbitrarily mutated at one to several amino acid residues by substitution, deletion, addition or/and insertion, and which inhibits the biological actions of the Fas/Fas ligand system, and in particular, the Fas-mediated apoptosis, with the binding activity to the Fas ligand retained. The Fas derivative may also comprise a mutant of Fas, Fas in a truncated form, a chimeric protein, a fusion protein, and a chemically modified Fas. The Fas from which the Fas derivative is derived may be the one derived from any animal species as long as its property is that described above, although use of the Fas of human origin is preferred in consideration of the antigenicity.

Exemplary Fas derivatives are the extracellular domain of a known Fas; a Fas from which the transmembrane domain has been deleted; a chimeric protein of the extracellular domain of a Fas and another protein such as human Fas-Fc which is a chimeric protein of the extracellular domain of human Fas and Fc fragment of human immunoglobulin. The Fas derivative may be the one prepared by any production process by utilizing known Fas sequences and known gene engineering techniques. For example, the process for producing the Fas-Fc is described in the Examples of International Patent Application Publication No. WO 95/13293.

Another preferable Fas derivative is the Fas having a deletion in its N terminal. A Fas derivative shFas(nd29)-Fc described in International Patent Application Publication No. WO 97/42319 is a derivative including the extracellular domain of the known human Fas from which N terminal sequence of from 1st to 29th amino acid has been deleted, and shFas(nd29)-Fc is a preferable example in view of its high activity.

The antisense oligonucleotide for the gene or the mRNA of the Fas or the Fas ligand is not limited to any particular sequence as long as it inhibits the expression of the Fas or the Fas ligand, and may be, for example, the antisense oligonucleotide of the Fas ligand disclosed in International Patent Application Publication No. WO 95/13293.

The preventive and therapeutic agent for inflammatory intestinal disease of the present invention is characterized by its inclusion of the anti-Fas ligand antibody as described above. The agent may be in the form of a pharmaceutical composition or kit wherein the apoptosis-suppressing substance is appropriately combined with at least one pharmaceutical carrier or medium such as sterilized water, physiological saline, a vegetable oil, a mineral oil, a higher alcohol, a higher fatty acid, or a nontoxic organic solvent; and optional additives such as an excipient, a colorant, an emulsifier, a suspending agent, a surfactant, a solubilizer, a nonadsorptive, a stabilizer, a preservative, an antioxidative, a buffer, an isotonizing agent, or a pain relieving agent. The agent may be administered either orally, or parenterally by intravenous, intracoronary, subcutaneous, intramuscular, percutaneous, intrarectal, or topical administration or by inhalation.

Preferably, the preventive and therapeutic agent of the present invention is parenterally administered by either systemic or topical, rapid or continuous administration.

The preventive and therapeutic agent of the present invention may be administered to a human at an appropriate dose. The dose may be determined by taking the conditions and the age of the patient as well as the administration route into consideration. For example, an adequate divided dose in the range of approximately 0.01 to 1,000 mg/kg may be selected in the case of systemic administration. The preventive and therapeutic agent for inflammatory intestinal disease of the present invention, however, is not limited to the administration route and the dose as described above. The anti-Fas ligand antibody or the humanized anti-Fas ligand antibody may be used in combination with other antibodies and apoptosis-suppressing substances such as Fas antagonist and Fas/Fas ligand bond-suppressing reagent, or in combination with other drugs.

The preventive and therapeutic agent for inflammatory intestinal disease of the present invention may be formulated into a pharmaceutical preparation in a normal process. For example, an injection may be prepared by dissolving the purified anti-Fas ligand antibody or the humanized anti-Fas ligand antibody in a medium such as physiological saline or a buffer and optionally supplementing the solution with an additive such as an anti-adsorptive. The preparation may also be in the form of a lyophilizate which is to be reconstituted before its use, and may contain any of the excipients that are generally used for facilitating the lyophilization.

The anti-Fas ligand antibody used in the preventive and therapeutic agent for inflammatory intestinal disease of the present invention exhibits effects of improving organ and tissue disorders in inflammatory intestinal disease models, in particular, in the model of TNBS(2,4,6-trinitro benzene sulfonic acid)-induced inflammatory intestinal disease as shown in Examples. More specifically, the preventive and therapeutic agent of the present invention exhibits the effects of improving mucous lesion, intestine adhesion, and diarrhea in the model of the TNBS-induced inflammatory intestinal disease in the increment (active) stage. It should be noted that, in the Examples, an antibody against the Fas ligand from rodent (an anti-mouse Fas ligand antibody) is used in the demonstration of the therapeutic and prophylactic effects since the models used in the experiments are rodent (rat) models. Equivalent inhibitory effects may be expected for the anti-human Fas ligand antibody and the humanized anti-human Fas ligand antibody when used in human.

The preventive and therapeutic agent for inflammatory intestinal disease of the present invention exhibits no toxicity as demonstrated in the following Examples, and therefore, it can be used safely. In view of such situation, the preventive and therapeutic agent for inflammatory intestinal disease of the present invention is expected to exhibit prophylactic or therapeutic effects for those suffering from the inflammatory intestinal disease. Preferably, the preventive and therapeutic agent of the present invention is expected to exhibit therapeutic action for the inflammatory intestinal disease in its active stage, and more preferably, to exhibit the effects of improving mucous lesion, intestine adhesion, and diarrhea in the active stage of the inflammatory intestinal disease.

EXAMPLES

Next, the present invention is described in further detail by referring to Examples which are given by way of examples and not by way of limiting the scope of the present invention. The abbreviations used in the following description are those commonly used in the art.

The production process and the apoptosis-suppressing activity of the anti-Fas ligand antibody and the humanized anti-Fas ligand antibody of the present invention are disclosed in International Patent Application Publication WO 97/02290.

Example 1

Production of Anti-mouse Fas Ligand Antibody and its Purification (1) Production of Anti-mouse Fas Ligand Antibody A plasmid containing human elongation factor (EF) promoter, and in its downstream, the gene coding for the chimeric protein prepared by fusing the extracellular domain of mouse Fas ligand from soluble mouse Fas ligand WX2 (J. Immunology, vol. 157, pages 3918–3924, 1996) and the cytoplasmic domain, the transmembrane domain, and a part of the extracellular domain (from N terminal to 78th amino acid) of mouse CD40 ligand was prepared (Mizushima-Nagata, Nucleic Acids Research, vol. 18, page 5322, 1990). The plasmid was transfected in WR19L cell to obtain a recombinant cell W40LFL expressing the mouse Fas ligand on its cell membrane for use as the antigen to be administered. Armenian hamsters were used for the animals to be immunized. The Armenian hamsters were subcutaneously administered with $1 \times 10^7$ W40LFL mixed with Freund complete adjuvant, and one month later, subcutaneously administered with $2 \times 10^7$ W40LFL suspended in PBS, and in another one month later, administered with $5 \times 10^6$ W40LFL suspended in PBS from their foot pad. 3 days after the administration, lymph node cells were collected and fused with mouse myeloma cell P3-X63-Ag8-U1 (P3-U1). After selecting the hybridoma by HAT medium (hypoxanthine-aminopterin-thymidine), hybridoma FLIM58 whose supernatant had neutralizing activity for cytotoxicity of mouse Fas ligand was obtained from the survived hybridomas.

(2) Production of FLIM58 and Its Purification

Hybridoma FLIM58 was cultivated in serum-free medium Hybridoma-SFM (GIBCO BRL), and the culture supernatant was purified by protein A column (PROSEP-A, Bioprocessing) to obtain purified antibody FLIM58. Concentration of the protein was calculated from absorbance at 280 nm.

Example 2

Toxicity Study of the Anti-mouse Fas Ligand Antibody FLIM58

(1) Method

Male, 8 week old DBA/1J mice and C3H/He mice (Charles River Japan ) were used. The mice were administered from their tail vein with the anti-mouse Fas ligand antibody FLIM58 at a dose of 100 mg/30 ml/kg. The control group was administered from their tail vein with physiological saline at a dose of 30 ml/kg. The group consisted three animals for both strains. Observation period was 7 days, and body weight measurement, hematological tests (red blood cell, white blood cell, platelet), and hematobiological tests (GOT, GPT, urea nitrogen), and autopsy with naked eye were conducted.

(2) Results

The body weight increase, the hematological test values (red blood cell, white blood cell, platelet), and the hematobiological test values (GOT, GPT, urea nitrogen) of the group administered with the anti-mouse Fas ligand antibody FLIM58 were not significantly different from those of the control group. In addition, no abnormalities were found in the group administered with the anti-mouse Fas ligand antibody FLIM58 by the autopsy with naked eye.

Example 3

Effects of Administration of Anti-mouse Fas Ligand Antibody FLIM58 in the TNBS-induced Inflammatory Intestinal Disease Model (1) Method Male, 6 week old Wistar rats (Charles River Japan) were administered with 0.1 ml solution of 120 mg/ml TNBS (Wako Pure Chemicals) in 50% ethanol by rectal infusion using an oral sound for rat (manufactured by Natsume Seisakusho, KN-349A) at a position 7 cm from anus (day 0). On the next day (day 1), the animals were administered from their tail vein with the anti-mouse Fas ligand antibody FLIM58 at a dose of 3 or 10 mg/5 ml/kg. Autopsy was conducted at 8th day (day 8) to determine lesion score and colorectal weight. In determining the lesion score, lesion in the mucous membrane, adhesion of the large intestine with other intestinal tubes, and diarrhea of the colorectal content were scored in accordance with the criteria as described below, and the scores were summed to obtain the total score (Gastroenterology, vol. 96, pages 795–803, 1989; Shokakito Men-eki (Digestive Apparatus and Immunology), vol. 30, pages 128–133, 1995). The control group was administered from their tail vein with physiological saline at a dose of 5 ml/kg instead of the FLIM58. Each group consisted 6 animals.

Lesion in the mucous membrane

| | |
|---|---|
| Score 0 | Normal |
| Score 1 | Regional inflammation at one position (congestion or hypertrophy, and no ulcer) |
| Score 2 | Linear ulcer associated with no serious inflammation |
| Score 3 | Ulcer with inflammation at one position |
| Score 4 | Ulcer or inflammation at two or more positions (ulcer at least at one position) |
| Score 5 | Ulcer and inflammation at two or more positions, or ulcer and inflammation with axial length of at least 1 cm |

Adhesion of the large intestine with other intestinal tubes

| | |
|---|---|
| Score 0 | Adhesion unrecognizable |
| Score 1 | Adhesion recognized |

Diarrhea of the colorectal content

| | |
|---|---|
| Score 0 | Diarrhea unrecognizable |
| Score 1 | Diarrhea recognized |

(2) Results

Figure 2:
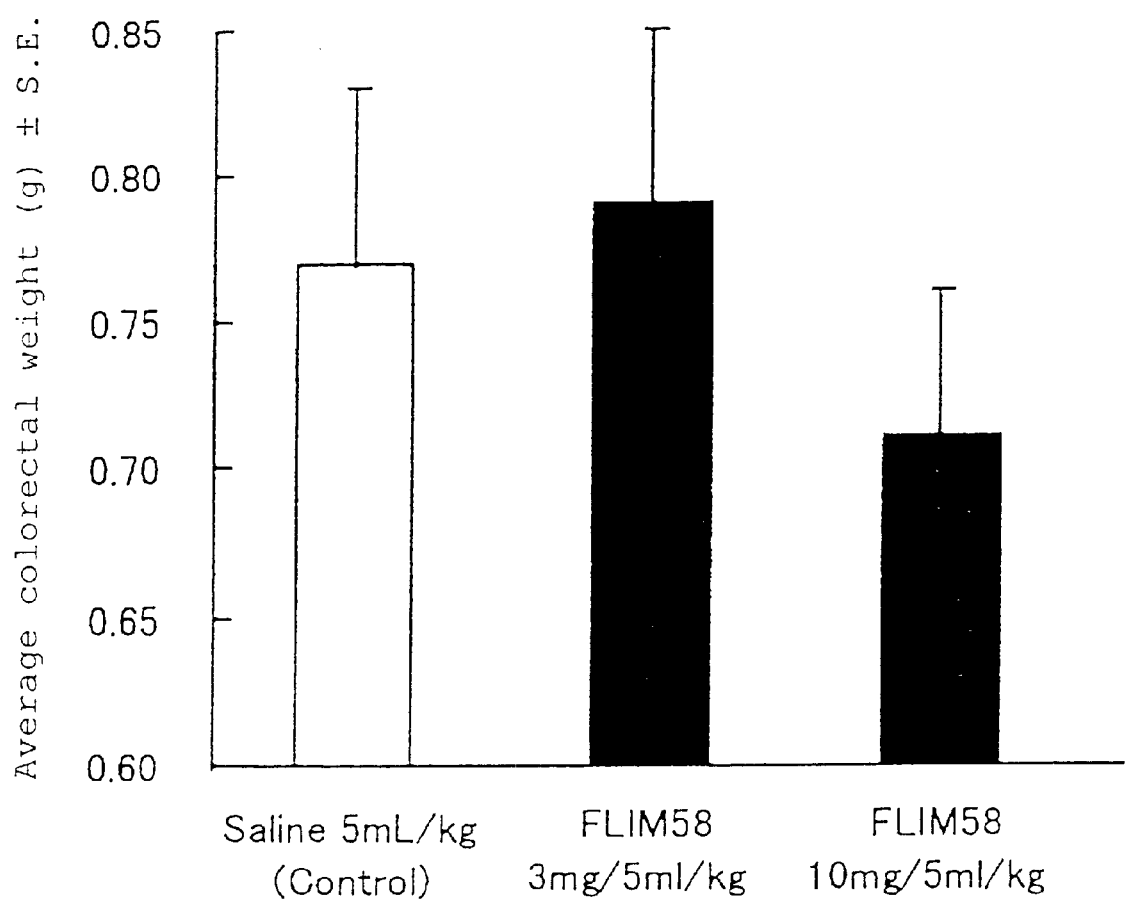
FIG. 2 is a view showing the effects of the anti-mouse Fas ligand antibody in improving the tissue disorder of the model for the inflammatory intestinal disease. The white column and the black column stand for the control group and the group administered with the anti-mouse Fas ligand antibody, respectively.

As shown in FIG. 1, the lesion score of the group administered with 3 or 10 mg/kg of FLIM58 was lower than that of the control group. As shown in FIG. 2, no significant difference in the colorectal weight was noted between the group administered with 3 mg/kg of FLIM58 and the control group, while the group administered with 10 mg/kg of FLIM58 showed less colorectal weight compared to the control group. cl INDUSTRIAL APPLICABILITY The preventive and therapeutic agent for inflammatory intestinal disease of the present invention contains an anti-Fas ligand antibody as its effective component. Therefore, it has the action of suppressing the apoptosis, and hence, the effects of preventing or treating the biological actions such as Fas-mediated cell death where Fas/Fas ligand system is involved, and inflammatory intestinal disease wherein apoptosis is involved. The anti-Fas ligand antibody of the present invention is highly expected for use in prophylactic and therapeutic treatments of the inflammatory intestinal disease wherein the Fas-mediated cell death and other apoptotic mechanisms are involved.

What is claimed is:

1. A method for preventing and treating an inflammatory intestinal disease by administering an effective amount of anti-Fas ligand antibody.

2. A method according to claim 1, wherein said disease is selected from the group consisting of Crohn's disease and ulcerative colitis.

3. A method according to claim 1, wherein said disease is induced by chemicals.

4. A method according to claim 1, wherein said method has improved at least one symptom selected from the group consisting of mucous lesion, intestine adhesion and diarrhea.

5. A method according to claim 1, wherein said anti-Fas ligand antibody is a humanized anti-Fas ligand antibody.

6. A method for preventing and treating at least one disease selected from the group consisting of inflammatory intestinal disease induced by infection, drugs, chemicals and radiation, ischemic colitis, and idiopathic inflammatory intestinal disease by administering an anti-Fas ligand antibody.

* * * * *